US00PP35829P2

(12) United States Plant Patent
Caster et al.

(10) Patent No.: US PP35,829 P2
(45) Date of Patent: May 28, 2024

(54) BLUEBERRY PLANT NAMED 'DRISBLUETHIRTY'

(50) Latin Name: ***Vaccinium corymbosum* L.**
Varietal Denomination: DrisBlueThirty

(71) Applicant: Driscoll's, Inc., Watsonville, CA (US)

(72) Inventors: Brian K. Caster, Prunedale, CA (US); Jennifer K. Izzo, Watsonville, CA (US); Bruce D. Mowrey, Asheville, NC (US); Sarah Wool, Santa Paula, CA (US); James Olmstead, Aptos, CA (US)

(73) Assignee: Driscoll's, Inc., Watsonville, CA (US)

( * ) Notice: Subject to any disclaimer, the term of this patent is extended or adjusted under 35 U.S.C. 154(b) by 9 days.

(21) Appl. No.: 18/141,906

(22) Filed: May 1, 2023

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

(56) References Cited

U.S. PATENT DOCUMENTS

PP6,699 P 3/1989 Wood
PP11,807 P2 3/2001 Lyrene
PP12,783 P2 7/2002 Lyrene
PP15,146 P3 9/2004 Hancock
PP19,503 P3 11/2008 Lyrene
PP20,436 P2 10/2009 Caster et al.
PP20,449 P2 11/2009 Caster et al.
PP20,488 P2 11/2009 Caster et al.
PP24,407 P3 4/2014 Caster et al.
PP24,489 P3 5/2014 Lyrene et al.
PP24,568 P3 6/2014 Caster et al.
PP24,569 P3 6/2014 Caster et al.
PP24,605 P3 7/2014 Caster et al.
PP26,287 P3 1/2016 Caster et al.
PP26,451 P3 3/2016 Rodriguez et al.
PP26,537 P3 3/2016 Caster et al.
PP26,643 P3 4/2016 Caster et al.
PP26,748 P3 5/2016 Rodriguez et al.
PP27,622 P3 1/2017 Caster et al.
PP28,933 P2 2/2018 Caster et al.
PP31,649 P2 4/2020 Caster et al.
PP31,650 P2 4/2020 Caster et al.
PP31,685 P2 4/2020 Mowrey et al.
PP31,698 P2 4/2020 Mowrey et al.
PP32,267 P2 10/2020 Caster et al.
PP32,744 P3 1/2021 Caster et al.
PP32,876 P2 3/2021 Mowrey et al.
PP33,066 P2 5/2021 Mowrey et al.
PP33,718 P2 12/2021 Caster et al.
PP34,067 P2 3/2022 Caster et al.
PP34,179 P2 5/2022 Mowrey et al.
PP34,316 P2 6/2022 Mowrey et al.

*Primary Examiner* — Susan McCormick Ewoldt
(74) *Attorney, Agent, or Firm* — Morrison & Foerster LLP

(57) ABSTRACT

A new and distinct variety of blueberry plant named 'DrisBlueThirty', particularly selected as a late and concentrated spring variety with high fruit quality, flavor, and average size, that can be grown under evergreen or mid-chill dormant conditions, is disclosed.

8 Drawing Sheets

Latin name: Botanical classification: *Vocciniitni corymbosum* L.

Varietal denomination: The varietal denomination of the claimed variety of blueberry plant is 'DrisBlueThirty'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueThirty'.

Blueberry plant variety 'DrisBlueThirty' was selected in Santa Cruz County. California in July 2008 and originated from a controlled cross between the proprietary female parent blueberry plant '127D 2' (unpatented) and the male parent blueberry plant 'DrisBlueFour' (U.S. Plant Pat. No. 24,407). The original seedling of the new variety was first asexually propagated via softwood cuttings in Santa Cruz County, California in August 2009.

'DrisBlueThirty' was subsequently asexually propagated via softwood cuttings and underwent further testing in Ventura County, California for seven years (2011 to 2018). The present blueberry variety has been found to be stable and reproduce true to type through successive asexual propagations via softwood cuttings and tissue culture.

'DrisBlueThirty' was selected as a late and concentrated spring variety with high fruit quality, flavor, and average size, that can be grown under evergreen or mid-chill dormant conditions.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are six and a half years old, unless otherwise specified.

DETAILED BOTANICAL DESCRIPTION

Figure 1:
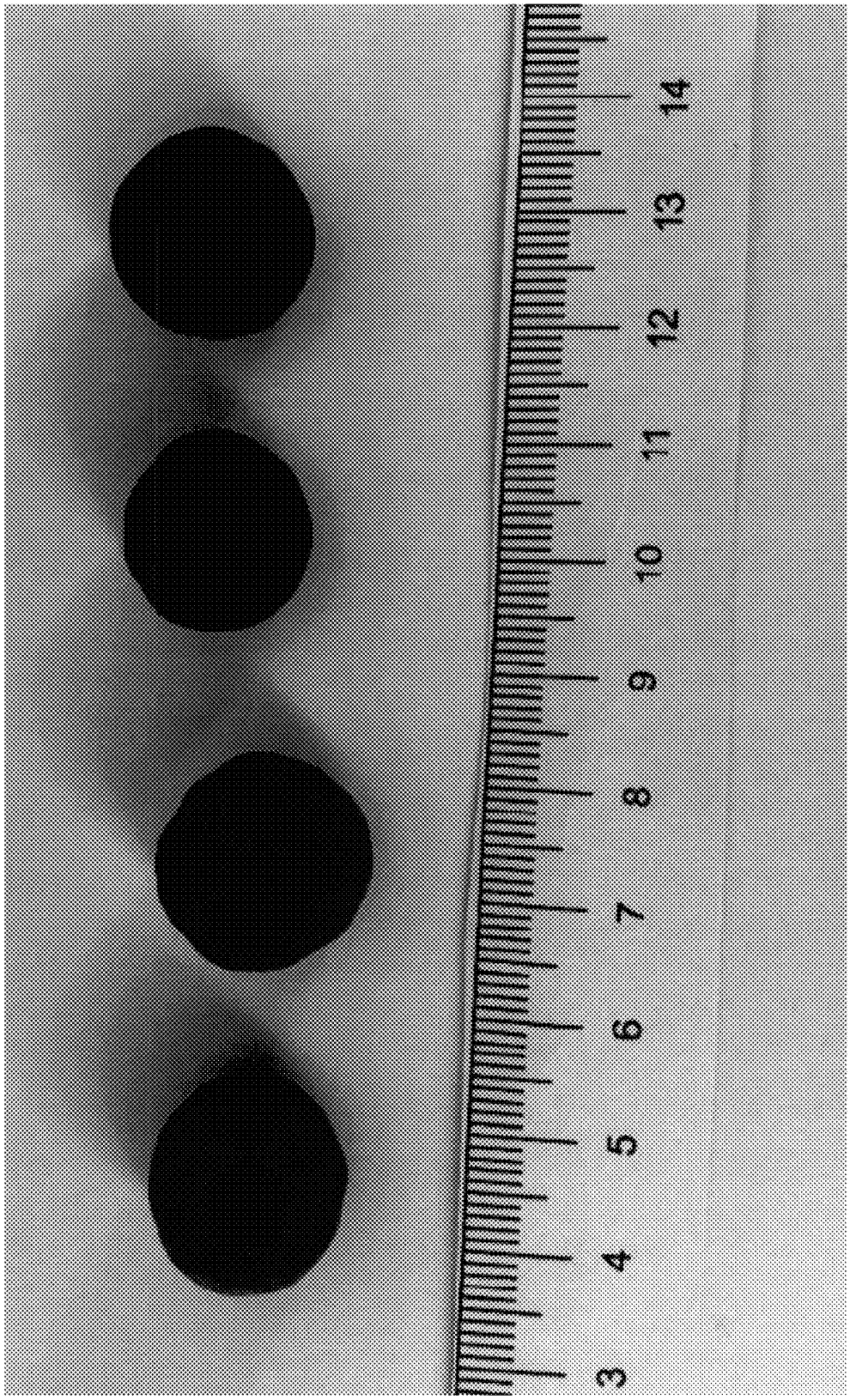
FIG. 1 illustrates whole fruit of variety 'DrisBlueThirty'. From left to right: calyx side up with bloom; pedicel side up with bloom; calyx side up without bloom; and pedicel side up without bloom.
Figure 2:
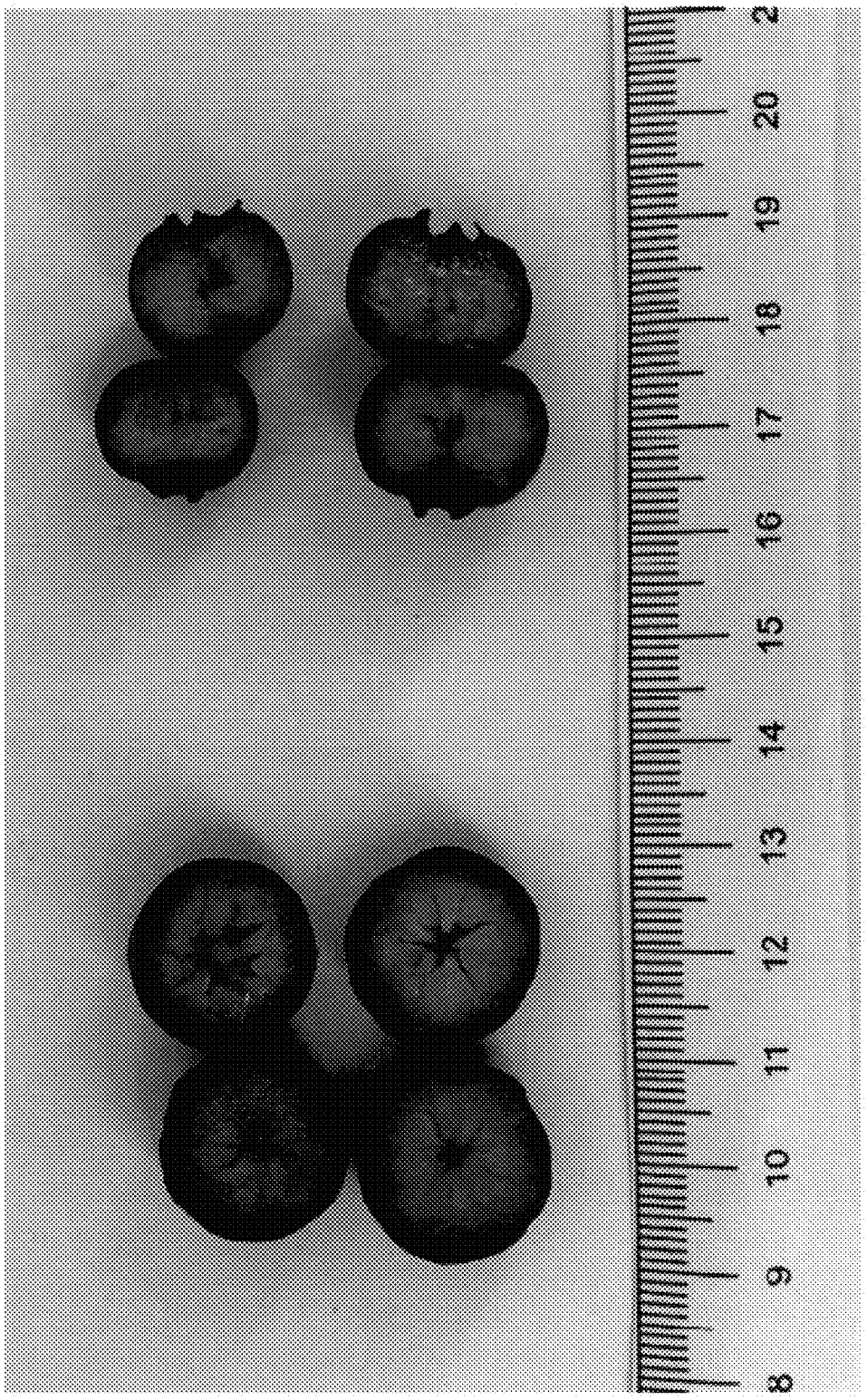
FIG. 2 illustrates transverse (left) and longitudinal (right) cross sections of fruit of variety 'DrisBlueThirty'.
Figure 3:
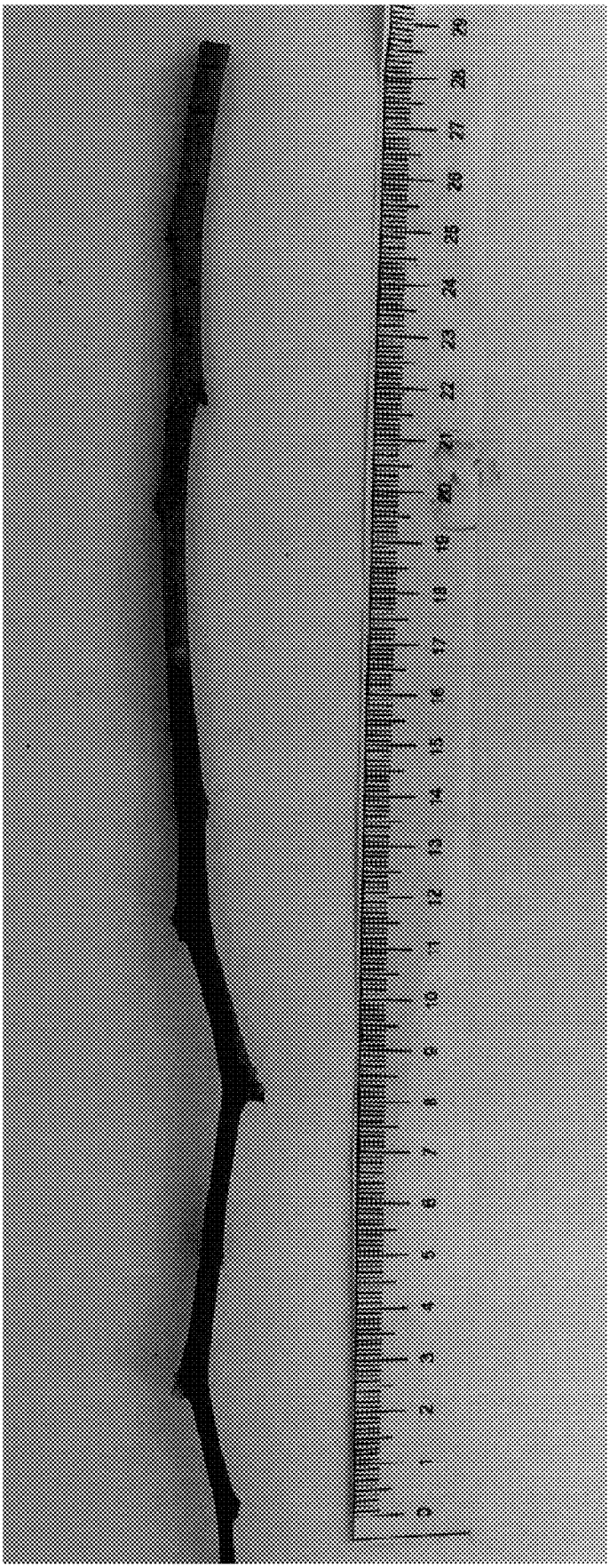
FIG. 3 illustrates a section of a cane of variety 'DrisBlueThirty'.
Figure 4:
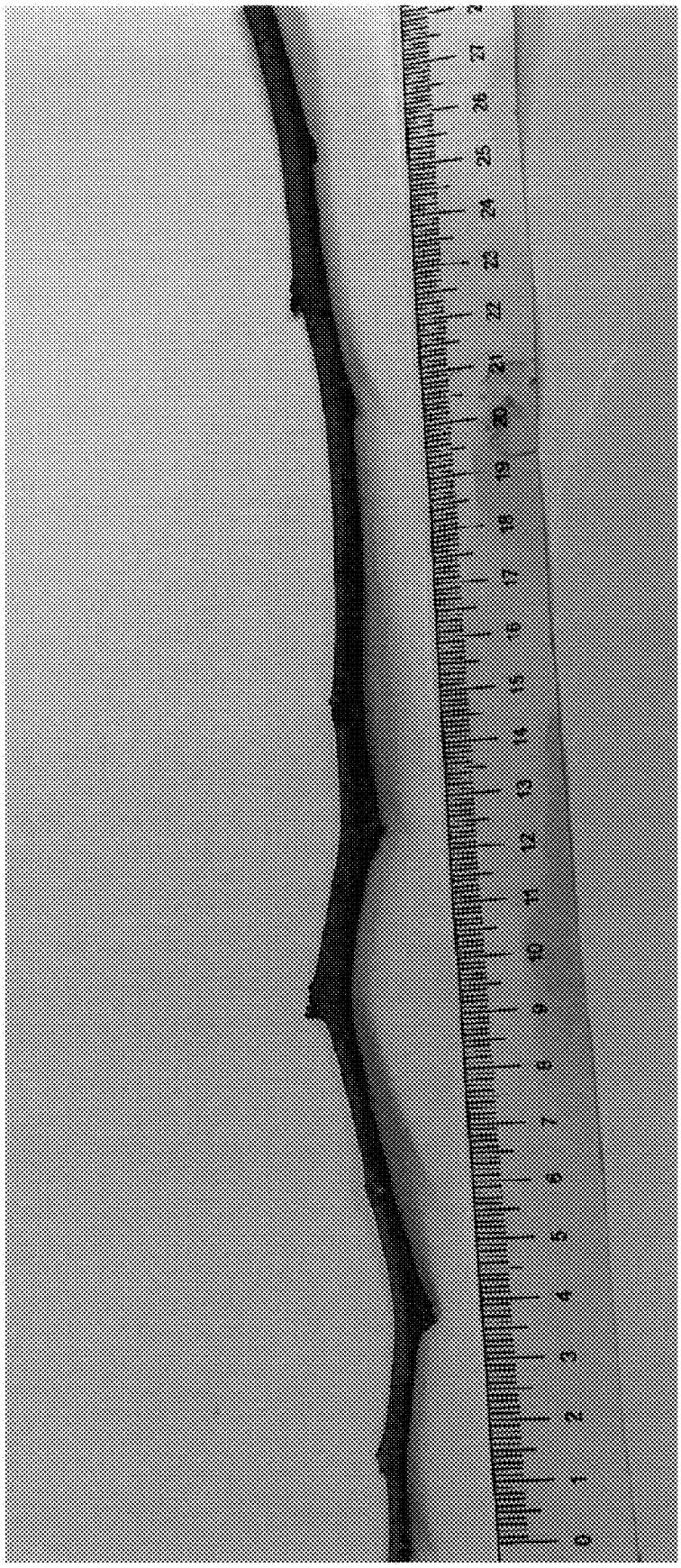
FIG. 4 illustrates another view of a section of a cane of variety 'DrisBlueThirty'.
Figure 5:
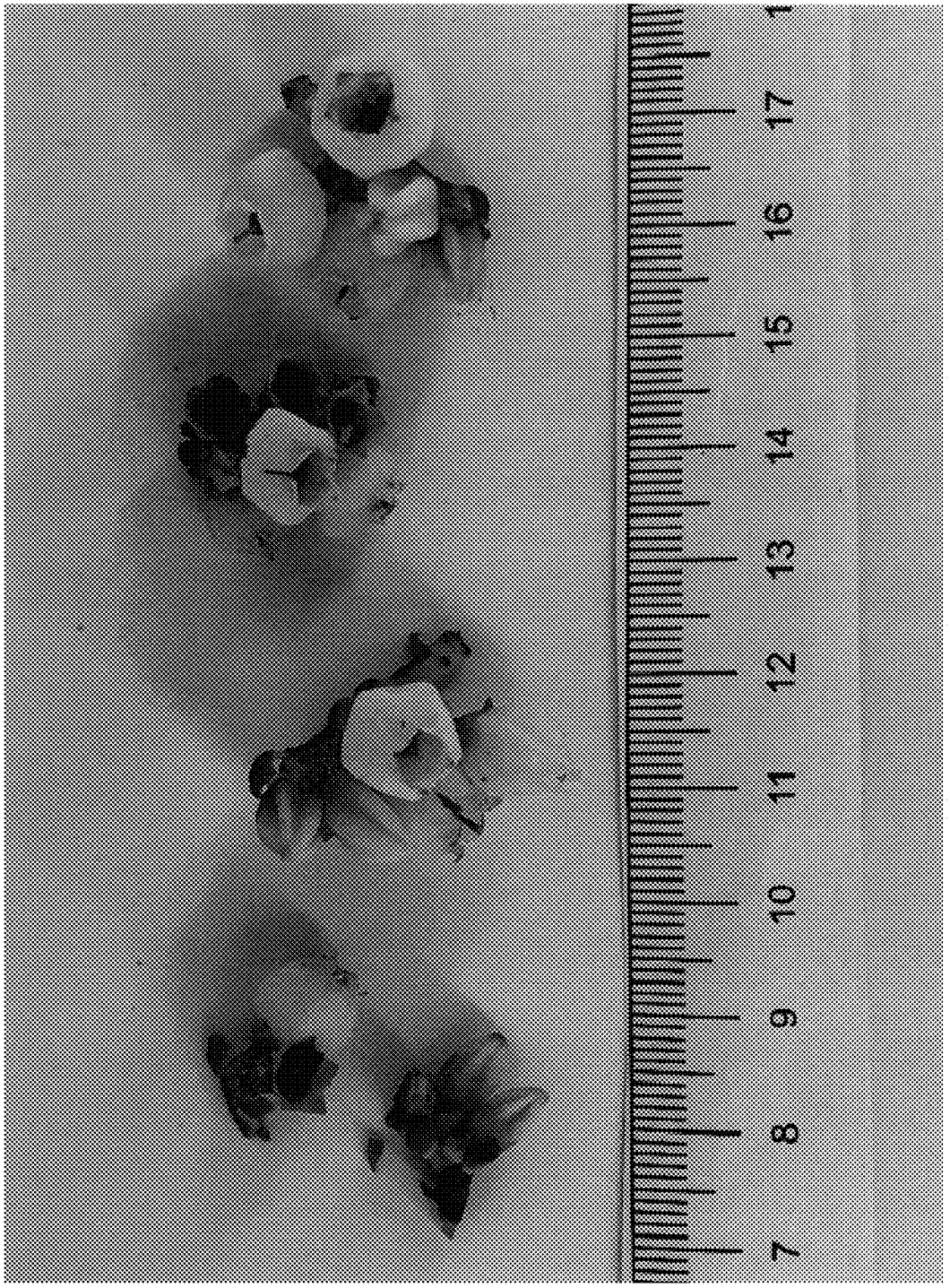
FIG. 5 illustrates clusters of flowers of variety 'DrisBlueThirty'.
Figure 6:
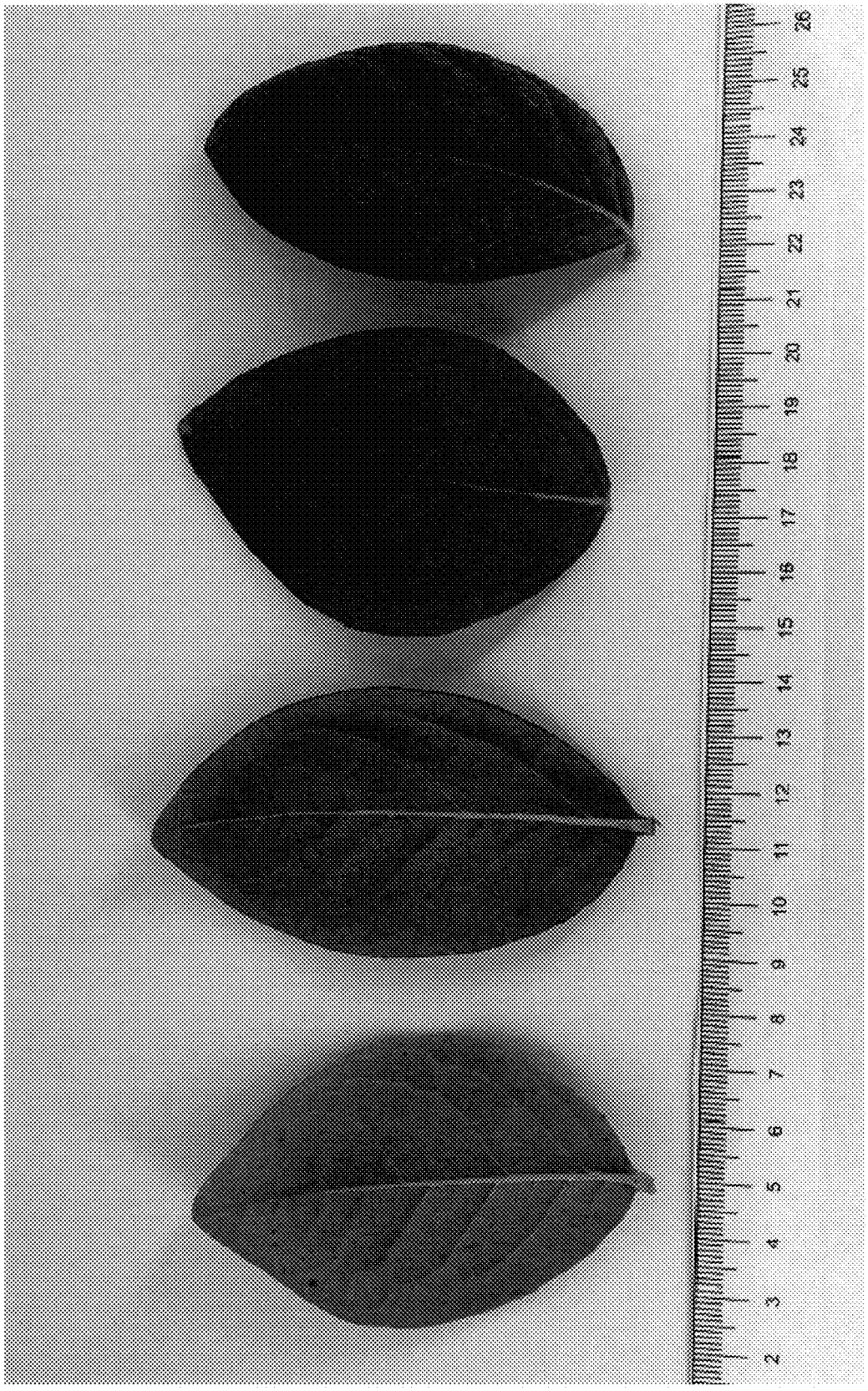
FIG. 6 illustrates the lower surface (left) and upper surface (right) of leaves of variety 'DrisBlueThirty'.
Figure 7:
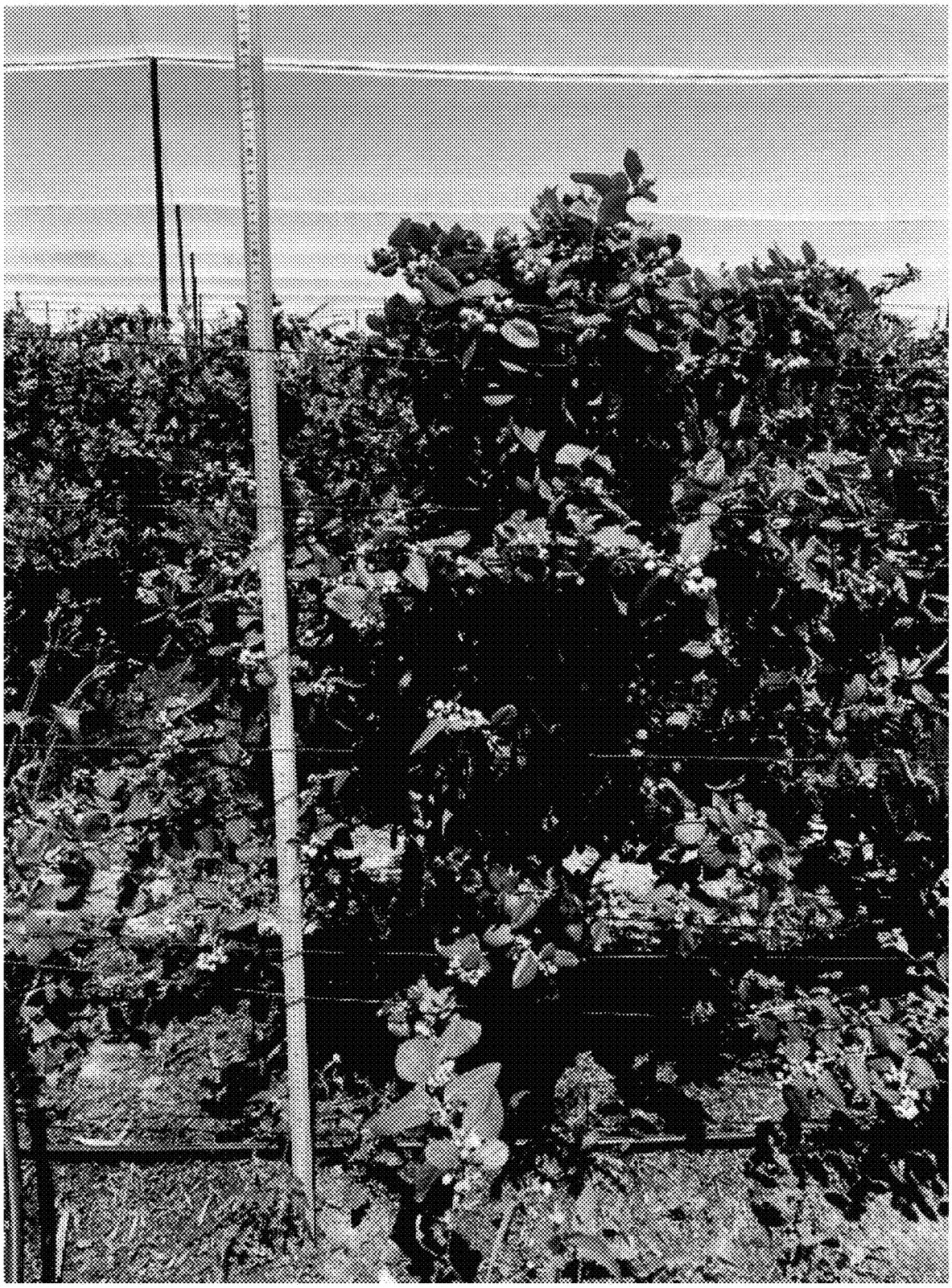
FIG. 7 illustrates a whole plant of variety 'DrisBlueThirty'.
Figure 8:
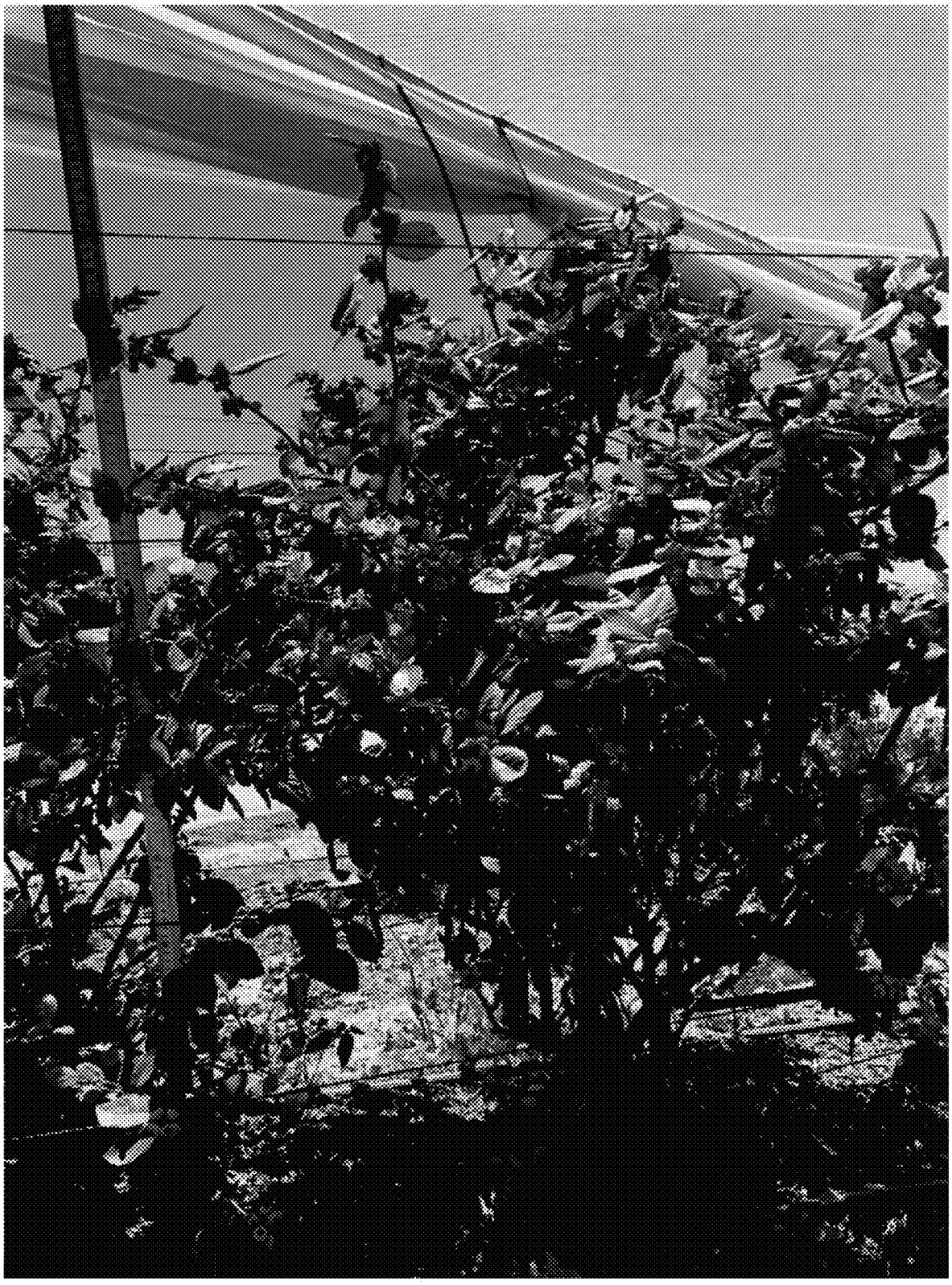
FIG. 8 illustrates another view of a whole plant of variety 'DrisBlueThirty'

The following description sets forth the distinctive characteristics of 'DrisBlueThirty'. The data which define these characteristics is based on observations taken in Ventura County, California from 2011 to 2018. This description is in accordance with UPOV terminology. Color designations, color descriptions, and other phenotypical descriptions may deviate from the stated values and descriptions depending upon variation in environmental, seasonal, climatic and cultural conditions. 'DrisBlueThirty' has not been observed under all possible environmental conditions. Unless noted otherwise, the botanical description of 'DrisBlueThirty' was taken from plants that were six and a half years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family.*—Ericaceac.

*Botanical.*—*Vaccinium coumbosum* L.

*Common name.*—Blueberry.

*Variety name.*—'DrisBitieThirty'.

Parentage:

*Female parent.*—Proprietary blueberry plant '127D 2' (unpatented).

*Male parent.*—'DrisBlueFour' (U.S. Plant Pat. No. 24,407).

Plant:

*Height.*—129.3 cm.

*Width.*—134.3 cm.

*Length/width ratio.*—~1.0.

*Vigor.*—Medium.

*Growth habit.*—Semi-upright.

*Chilling requirements.*—'DrisBlueThirty' can be grown under evergreen or mid-chill dormant conditions.

*Time of vegetative bud burst.*—Medium.

*One-year-old shoot* (*young canes*).—Length: 47 cm. Diameter at the base: 9 mm. Diameter at the tip: 3 mm. Internode length on the upper half: 17.8 mm. Color: RHS N144A. (Strong yellowish green).

*Five-year-old shoot* (*mature canes*).—Length: 88 cm. Diameter at the base: 27 mm. Diameter at the tip: 13 mm.

Leaves:

*Length.*—67.3 mm.

*Width.*—42.3 mm.

*Length/width ratio.*—1.6.

*Internode length.*—25.23 mm.

*Shape.*—Ovate.

*Margin.*—Entire.

*Arrangement.*—Alternate.

*Color on upper side.*—RHS 147A (Moderate olive green).

*Color on lower side.*—RHS 191B (Greyish yellow green).

*Vein color.*—RHS 148D (Greyish yellow green).

*Venation pattern.*—Reticulate.

*Glaucosity on upper side.*—Weak.

*Petiole.*—Length: 4.0 mm. Diameter: 2.19 mm. Color: RHS 193A (Pale yellow green).

Flowers:

*Flower length* (*excluding pedicel*).—16.64 mm.

*Flower width.*—7.31 mm.

*Flower leng,th/width ratio.*—2.3.

*Flower bud.*—Length: 5 mm. Width: 4 mm. Number of flowers per bud: 3. Anthocyanin color: Weak. Overall color: RHS 157A (Pale yellow green).

*Flower pedicel.*—Length: 6.19 mm. Diameter: 1.26 mm. Color: RHS 142C (Light yellow green).

*Cololla.*—Shape: Urceolate. Color of corolla. tube: RHS 157A (Whitish green). Anthocyanin coloration of corolla tube on outer side: Absent. Conspicuousness of ridges on corolla tube: Absent. Color of receptacle: RHS 143C (Green). Diameter of corolla aperture: 3.99 mm. Petal width (ridge to ridge): 5.36 mm.

*Reproductive organs.*—Style length (including stigma): 7.37 mm.

*Flowering interval on one-year-old shoot.*—February to April.

*Flowering interval on current year's shoot.*—February to April.

Fruit:

*Length.*—12.52 mm.

*Width.*—15.80 mm.

*Length/width ratio.*—0.8.

*Weight.*—2.2 grams/fruit.

*Shape in longitudinal section.*—Oblate.

*Attitude of sepals.*—Semi-erect.

*Type of sepals.*—Straight.

*Calyx basin.*—Diameter: 6.37 mm. Depth: 1.22 mm. Diameter/depth ratio: 5.2.

*Infructescence* (*fruit cluster*).—Number of berries per cluster: 3.60. Density: Medium. Peduncle length: 12.64 mm.

*Fruit pedicel.*—Diameter: 2.36 mm.

*Color of unripe fruit.*—RHS 143C (Strong yellow green).

*Intensity of bloom.*—Medium.

*Color of skin after removal of bloom on mature fruit.*—RHS N186A (Dark purplish grey).

*Color of flesh.*—RHS 145C (Light yellow green).

*Fruit firmness.*—Firm.

*Sweetness.*—Medium.

*Acidity.*—Low.

*Seeds.*—Color: RHS 166C (Brownish orange).

*Fruiting.*—Fruiting type: On one-year-old and current season's shoots. Harvest interval on one-year-old shoot: April to June. Harvest interval on current year's shoot: April to June. Yield: 11,000 kg to 16,000 kg of fruit per hectare per season from 36 to 60-month old plants when grown at Ventura County, California.

Resistance to abiotic stress, pests, and diseases:

*Heat.*—Moderately resistant.

*Blueberry bud mite* (*Acalitus vaccini*).—Moderately resistant.

*Botiytis fruit rot* (*Botrytis cinerea*).—Moderately resistant.

COMPARISONS TO PARENTAL AND REFERENCE BLUEBERRY VARIETIES

'DrisBlueThirty' differs from the female parent proprietary blueberry plant '127D 2' (unpatented) in that 'DrisBlueThirty has a larger fruit size and firmer fruit texture that '127D 2'. 'DrisBlueThirty' also has the ability to produce fruit on both current season and one-year-old shoots.

'DrisBlueThirty' differs from the male parent and reference variety 'DrisBlueFour' (U.S. Plant Pat. No. 24,407) in that 'DrisBlueThirty' has short length of internodes on one-year-old shoots (upper half), broad leaf width, medium intensity of bloom on fruit, and bears fruit on both one-year-old and current season's shoots, whereas 'DrisBlueFour' has medium length of internodes on one--year-old shoots (upper half), medium leaf width, very strong intensity of bloom on fruit, and bears fruit on one-year-old shoots only.

'DrisBlueThirty' differs from the reference blueberry plant variety 'DrisBlueSeven' (U.S. Plant Pat. No. 24,605) in that 'DrisBlueThirty' has medium time of vegetative bud burst, anthocyanin coloration of corolla tube is absent, medium intensity of bloom on fruit, and bears fruit on both one-year-old and current season's shoots, whereas 'DrisBlueSeven' has very early time of vegetative bud burst, weak anthocyanin coloration of corolla tube, very strong intensity of bloom on fruit, and bears fruit on one-year-old shoots only.

What is claimed is:

1. A new and distinct variety of blueberry plant designated 'DrisBlueThirty' as shown and described herein.

* * * * *